United States Patent
Yamamoto et al.

(10) Patent No.: US 7,390,372 B2
(45) Date of Patent: *Jun. 24, 2008

(54) PROCESS FOR ATTACHING INDICATOR ELEMENT TO DISPOSABLE GARMENT

(75) Inventors: Hiroki Yamamoto, Kagawa-ken (JP); Toshifumi Otsubo, Kagawa-ken (JP)

(73) Assignee: Uni-Charm Co., Ltd., Ehime-ken (JP)

( * ) Notice: Subject to any disclaimer, the term of this patent is extended or adjusted under 35 U.S.C. 154(b) by 538 days.

This patent is subject to a terminal disclaimer.

(21) Appl. No.: 11/015,819

(22) Filed: Dec. 20, 2004

(65) Prior Publication Data

US 2005/0098259 A1    May 12, 2005

Related U.S. Application Data

(63) Continuation of application No. PCT/JP03/09260, filed on Jul. 22, 2003.

(30) Foreign Application Priority Data

Aug. 15, 2002  (JP)  .............................. 2002-236946

(51) Int. Cl.
  *B32B 37/00*  (2006.01)
(52) U.S. Cl. .................. 156/164; 156/229; 156/269; 156/302
(58) Field of Classification Search ................. 156/160, 156/163, 164, 229, 250, 269, 290, 297, 302, 156/308.2, 308.4

See application file for complete search history.

(56) References Cited

U.S. PATENT DOCUMENTS

| 5,103,436 | A | 4/1992 | Yajika et al. |
| 6,017,406 | A | 1/2000 | Vogt |
| 6,440,239 | B1 | 8/2002 | Vogt |
| 6,558,499 | B1 | 5/2003 | Pargass et al. |
| 6,572,575 | B1 | 6/2003 | Shimada et al. |
| 6,788,803 | B2 | 9/2004 | Calvert |
| 2005/0067083 | A1 | 3/2005 | Vergona |

(Continued)

FOREIGN PATENT DOCUMENTS

EP    1 078 620 A2    2/2001

(Continued)

OTHER PUBLICATIONS

Supplementary European Search Report for EP 03 74 1527 issued Feb. 15, 2008.

*Primary Examiner*—James Sells
(74) *Attorney, Agent, or Firm*—Lowe Hauptman Ham & Berner LLP (57) ABSTRACT

In a process for attaching indicator elements onto a disposable garment, indication sheets with indicator elements and liquid-absorbent cores are fed onto inner and outer surfaces of an outer layer web. A rear half of the front one of the adjacent sheets is placed upon a front end zone of the core and a front half of the rear one of the adjacent sheets is placed upon a rear end zone of the core. The sheet is joined to the outer layer web, the core is joined to the inner and outer layer webs, and the webs are joined together. The sheet is cut together with the webs between the adjacent cores to form laminated panels with indicator elements in front and rear regions.

8 Claims, 8 Drawing Sheets

U.S. PATENT DOCUMENTS

| | | |
|---|---|---|
| 2005/0092427 A1 | 5/2005 | Vergona |
| 2005/0103436 A1 | 5/2005 | Otsubo et al. |

FOREIGN PATENT DOCUMENTS

| | | |
|---|---|---|
| EP | 1 552 802 A1 | 7/2005 |
| JP | 02-234760 | 9/1990 |
| JP | 04-161152 | 6/1992 |
| JP | 04-161152 A | 6/1992 |
| JP | 10-118116 | 5/1998 |
| JP | 2001-054536 | 2/2001 |
| JP | 2001-054536 A | 2/2001 |
| WO | 98/27906 A1 | 7/1998 |

PROCESS FOR ATTACHING INDICATOR ELEMENT TO DISPOSABLE GARMENT

BACKGROUND OF THE INVENTION

This invention relates to a process for attaching, in front and rear regions of a disposable garment such as a diaper comprising an outer layer web, an inner layer web and a liquid-absorbent core interposed between these inner and outer webs, indicator elements which are visually recognizable from the exterior of the outer layer web.

Japanese Patent Application Publication No. 2001-54536 A discloses a pull-on disposable diaper including a patterned sheet and a process for making the same. This diaper comprises a liquid-impervious backsheet lying on the side facing away from a wearer's body (outer layer web), a liquid-pervious topsheet (inner layer web) lying on the side facing the wearer's body, and a liquid-absorbent core interposed between these sheets. This diaper has a front waist region (front region), a rear waist region (rear region), a crotch region (intermediate region) extending between these waist regions, a waist-opening and a pair of leg-openings. The patterned sheet adapted to be visually recognizable from the exterior of the diaper is attached to an inner surface of the outer sheet.

The process for making this diaper comprises a step of attaching the patterned sheet in which the patterned sheet having an area smaller than the outer sheet is attached to the inner surface of the outer sheet at a predetermined location, a step of securing the core in which the core is secured to the inner surface of the outer sheet and a step of joining the sheets in which the inner sheet is placed upon and joined with the upper surface of the core. In the step of attaching the patterned sheet, a plurality of the patterned sheets are successively fed onto the inner surface of the outer sheet so as to be spaced one from another by a predetermined dimension in a longitudinal direction of the outer sheet and then these patterned sheets are attached to the outer sheet by means of a hot melt adhesive.

According to the process for making the diaper as disclosed in the above-cited Publication, a plurality of the patterned sheets must be individually fed onto and attached to the inner surface of the outer sheet with each pair of the patterned sheets being spaced apart from each other by a predetermined dimension in a transverse dimension. Feeding and attaching of these patterned sheets inevitably doubles time and labor and require the additional device as well as steps associated with such feeding as well as such attaching. Consequently, it is impossible to manufacture the diapers at a low cost.

SUMMARY OF THE INVENTION

It is an object of this invention to provide a process for attaching indicator elements all at once on surfaces front and rear regions of the laminated panel.

According to the present invention, there is provided a process for attaching, in front and rear regions of a disposable garment composed of a laminated panel which comprises an outer layer web lying on a side facing away from a wearer's body, an inner layer web lying on a side facing the wearer's body and a liquid-absorbent core interposed between the outer layer web and the inner layer web, a pair of indicator elements being visually recognizable from an exterior of the panel.

The process comprises the steps of feeding a plurality of indication sheets each extending in a machine direction and having the indicator elements in front and rear halves, at regular intervals onto a continuous first outer layer web running in the machine direction while feeding a plurality of the liquid-absorbent cores each extending in the machine direction and having a front end zone, a rear end zone and an intermediate zone, at regular intervals onto one of an inner surface of the continuous first outer layer web and an inner surface of the continuous inner layer web running in the machine direction; placing the intermediate zone of the core between each pair of the indication sheets adjacent to each other in the machine direction so that a rear half of a front one of the indication sheets adjacent to each other in the machine direction is placed upon the front end zone of the core, and a front half of a rear one of the indication sheets adjacent to each other in the machine direction is placed upon the rear end zone of the core;

joining the indication sheet to the first outer layer web, joining the core to at least one of the inner layer web and the outer layer web and joining inner surfaces of the inner layer web and the outer layer web overlaid; and forming the laminated panel by cutting the indication sheet together with the inner and outer layer webs in a cross direction between a pair of the cores adjacent to each other in the machine direction so that the indication sheet is divided into the front and rear halves to form a plurality of the laminated panels arranged in the machine direction and each having the indicator elements in the front and rear regions.

The present invention includes the following embodiments.

(1) The process for attaching indicator elements further includes the steps of placing an inner surface of a continuous second outer layer web running in the machine direction upon the outer surface of the first outer layer web and joining the first and second outer layer webs and wherein at the step of forming the laminated panel, the indication sheet is cut together with the first and second outer layer webs and the inner layer web in the cross direction between a pair of the cores adjacent to each other in the machine direction.

(2) The process for attaching indicator elements further includes the steps of attaching first stretchable elastic members lying between the cores adjacent to each other and extending in the cross direction and second stretchable elastic members lying on both lateral sides of the core and extending in the machine direction to the inner surface of the first outer layer web or the inner layer web in a stretched state.

(3) The process for attaching indicator elements further includes the steps of attaching first stretchable elastic members lying between the cores adjacent to each other and extending in the cross direction and second stretchable elastic members lying on both lateral sides of the core and extending in the longitudinal direction to the outer surface of the first outer layer web or the inner surface of the second outer layer web in a stretched state.

(4) The first and second outer layer webs are formed by one of a moisture-permeable and hydrophobic fibrous nonwoven fabric and a moisture-permeable and liquid-impervious plastic film and the inner layer web is formed by a hydrophilic fibrous nonwoven fabric.

(5) The indication sheet is formed by one of a moisture-permeable and hydrophobic fibrous nonwoven fabric and a moisture-permeable and liquid-impervious plastic film.

(6) The indicator elements comprise a pair of illustrations printed on the front and rear halves of the indication sheet and adjacent to each other in the machine direction.

(7) The illustrations are in mirror image relationship with each other in the machine direction.

DETAILED DESCRIPTION OF THE PREFERRED EMBODIMENTS

Details of the process according to this invention for forming the indicator element will be more fully understood from the description given hereunder with reference to the accompanying drawings.

Figure 1:
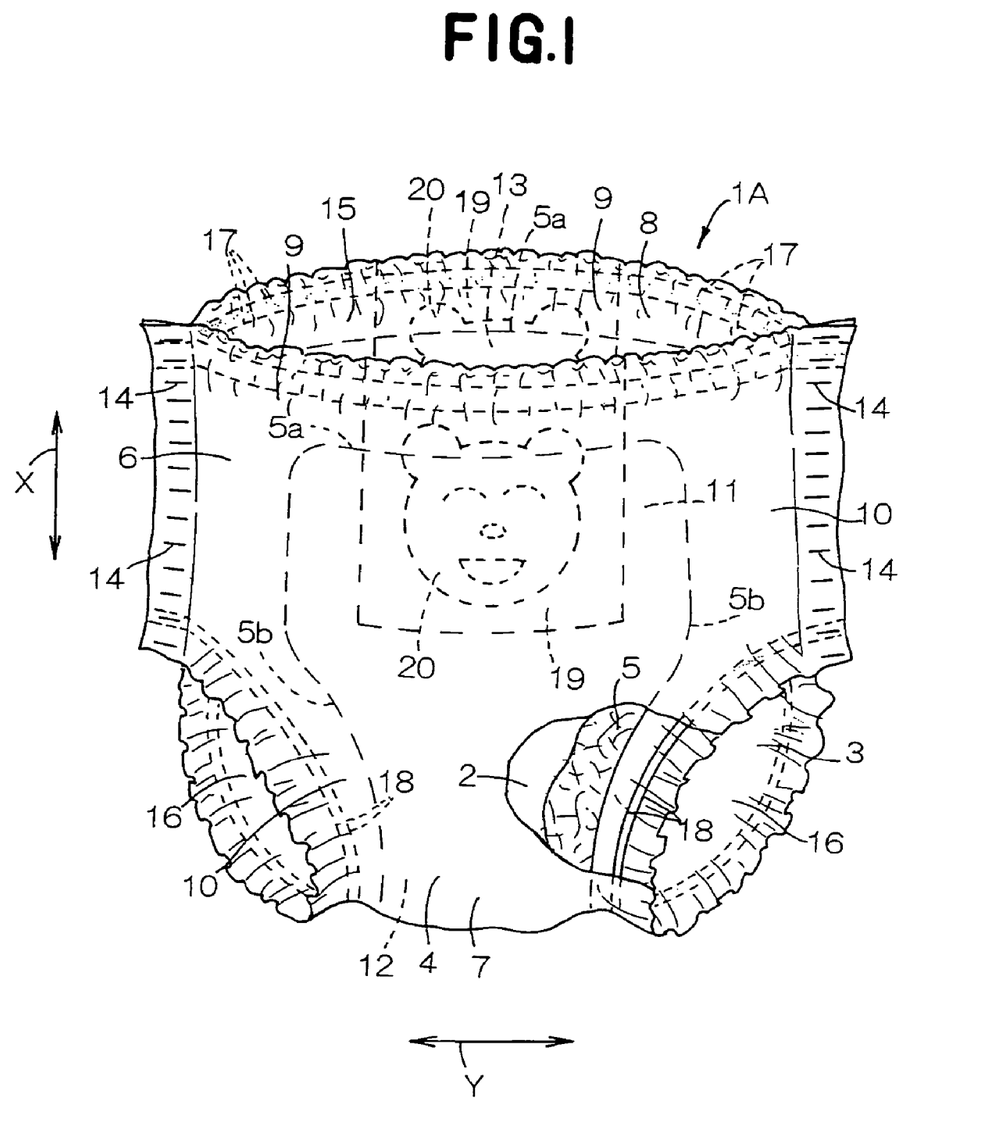
FIG. 1 is a partially cutaway perspective view showing a pull-on disposable diaper.
Figure 2:
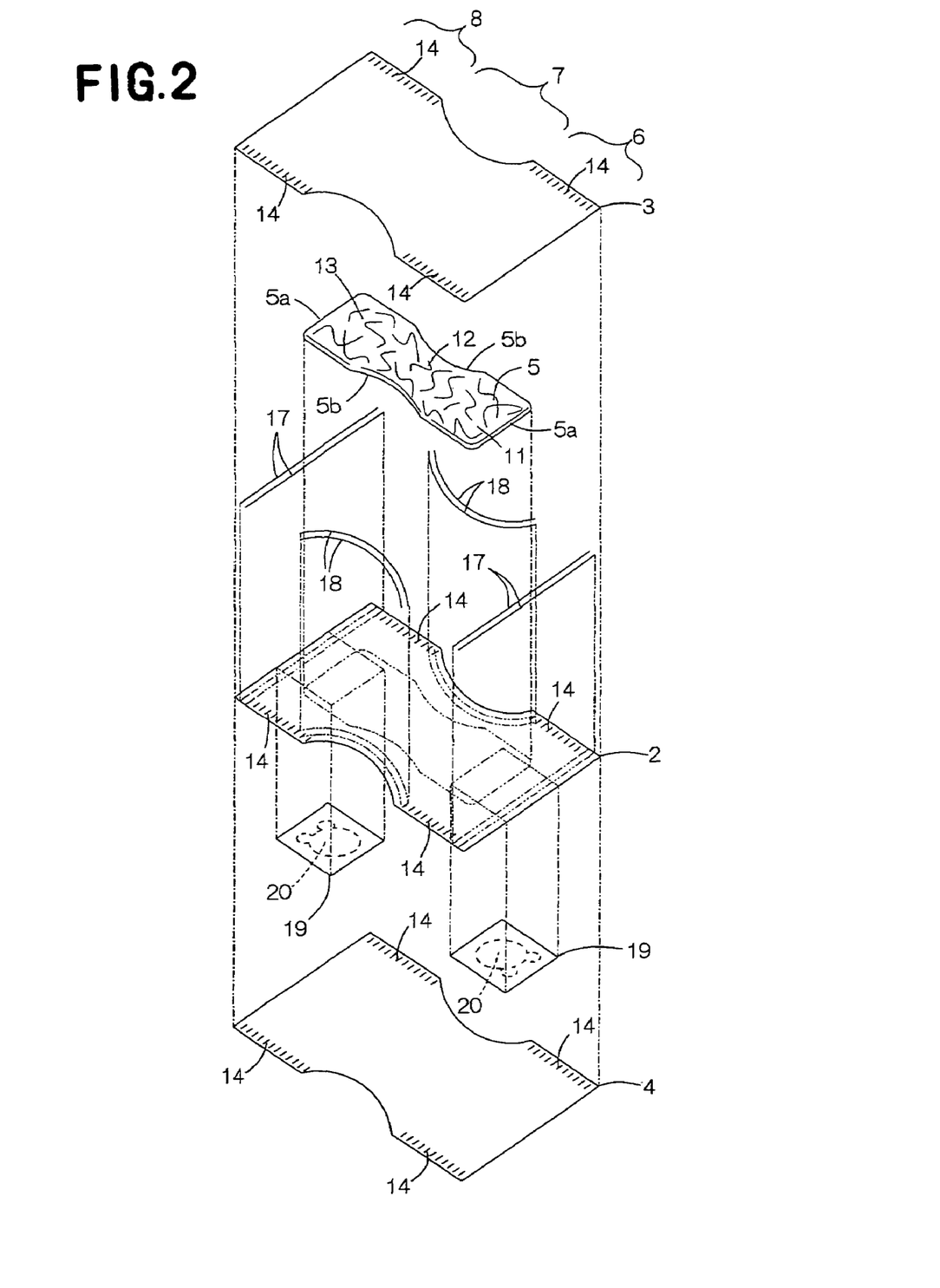
FIG. 2 is an exploded perspective view showing the diaper of FIG. 1.

FIG. 1 is a partially cutaway perspective view showing a pull-on disposable diaper 1A as an example of a disposable garment adopting the process according to this invention for arranging the indicator element and FIG. 2 is an exploded perspective view showing the diaper 1A of FIG. 1. In FIGS. 1 and 2, a vertical direction (longitudinal direction) is indicated by an arrow X and a transverse direction is indicated by an arrow Y. Expression "inner surfaces" of first and second backsheets 2, 4, a topsheet 3 and an indication sheet 19 refers to the surfaces these sheets facing a core 5 and expression "outer surfaces" of these sheets 2, 3, 4, 19 refers to the surfaces facing away from the core 5.

This diaper 1A comprises a laminated panel and is of pants-type and disposable after used. The diaper 1A comprises a liquid-impervious first backsheet 2 (first outer layer web) and a liquid-impervious second backsheet 4 (second outer layer web) both lying on the side facing away from a wearer's body, a liquid-pervious topsheet 3 (inner layer web) lying on the side facing the wearer's body and a liquid-absorbent core 5 interposed between the top- and backsheets 2, 3. The diaper 1A is composed of a front waist region 6 (front region) and a rear waist regions 8 (rear region) opposed to each other and a crotch region 7 (intermediate region) extending between these waist regions 6, 8. The diaper 1A has end flaps 9 lying outside longitudinally opposite ends 5a of the core 5 and extending in the transverse direction and side flaps 10 lying outside transversely opposite side edges 5b of the core 5 and extending in the longitudinal direction.

In the crotch region 7, the side flaps 10 describe circular arcs which are convex inwardly in the transverse direction of the diaper 1A. The diaper 1A has a generally hourglass-like planar shape when the diaper 1A is developed. The core 5 extends over the crotch region 7 into the front and rear waist regions 6, 8. The core 5 also has an hourglass-like shape and has front and rear end zones 11, 13 lying in the front and rear waist regions 6, 8, respectively, and an intermediate zone 12 lying in the crotch region 7.

In the diaper 1A, the side flaps 10 in the front and rear waist regions 6, 8 are overlaid and joined together by means of a plurality of heat-sealing lines 14 arranged intermittently in the longitudinal direction. The diaper 1A has a waist-opening 15 and a pair of leg-openings 16 lying below the waist-opening 15.

A plurality of waist elastic members (first stretchable elastic members) 17 extending in the transverse direction are contractibly attached to the end flaps 9. A plurality of leg elastic members (second stretchable elastic members) 18 extending in the longitudinal direction are contractibly attached to the side flaps 10 in the crotch region 7. These elastic members 17, 18 are interposed between the first backsheet 2 and the topsheet 3.

The first backsheets 2 is formed by moisture-permeable and hydrophobic fibrous nonwoven fabric. The second backsheet 4 is formed by moisture-permeable and liquid-impervious plastic film. The topsheet 3 is formed by hydrophilic fibrous nonwoven fabric. The core 5 comprises a mixture of fluff pulp and super-absorbent polymer particles or a mixture of fluff pulp, super-absorbent polymer particles and thermoplastic synthetic resin fibers, in any case, compressed to a desired thickness. The core 5 is preferably covered entirely with a liquid-pervious sheet such as a tissue paper or a hydrophilic fibrous nonwoven fabric in order to prevent the core 5 from getting out of its initial shape and/or to prevent the polymer particles from falling off.

The front and rear waist regions 6, 8 are provided in respective transversely middle zones thereof with indication sheets 19 each having an indicator element 20 adapted to be visually recognized from an exterior of the diaper 1A. The indication sheet 19 is made of moisture-permeable and liquid-impervious plastic film. The indicator element 20 comprises an illustration of a bear's face printed on an outer surface of the indication sheet 19. The indicator elements 20 are placed in the front and rear end zones 11, 13 of the core 5, respectively. The indicator element 20 is not limited to such an illustration but may be in the form of pattern, letters or figures.

Alternatively, the front waist region 6 is provided in its transversely middle zone with the indication sheet 19 printed with an illustration while the rear waist region 8 is provided in its transversely middle zone with the indication sheet 19 printed with letters. It is also possible to provide the front waist region 6 in its transversely middle zone with the indication sheet 19 printed with an illustration of a bear's face and to provide the rear waist region 8 in its transversely middle zone with the indication sheet 19 printed with an illustration of a horse' face.

The end flaps 9 are formed by respective portions of the first and second backsheets 2, 4 and the topsheet 3 extending outward in the longitudinal direction beyond the longitudinally opposite ends 5a of the core 5. The side flaps 10 are formed by respective portions of the first and second backsheets 2, 4 and the topsheet 3 extending outward in the transverse direction beyond the transversely opposite side edges 5b of the core 5.

The second backsheet 4 is placed on and intermittently joined to the outer surface of the first backsheet 2 by means of a hot melt adhesive (not shown). The indication sheet 19 is interposed between the first and second backsheets 2, 4 and has its inner surface intermittently joined to the outer surface of the backsheet 2 by means of a hot melt adhesive (not shown) The indication sheet 19 is left free from the backsheet 4.

In the end flaps 9 as well as in the side flaps 10, the first backsheet 2 and the topsheet 3 are overlaid and have the respective inner surfaces intermittently joined by means of hot a melt adhesive (not shown). The core 5 and the elastic members 17, 18 are intermittently attached to the first backsheet 2 and the topsheet 3 by means of a hot melt adhesive (not shown).

The adhesive is applied on the entire inner and outer surfaces of the first backsheet 2 and the entire inner surface of the topsheet 3. It is possible to coat the entire inner surface of the second backsheet 4 also with the adhesive. In this case, the outer surface of the indication sheet 13 is permanently joined to the inner surface of the second backsheet 4.

The pattern in which the adhesive is applied on the first backsheet 2 and the topsheet 3 is preferably selected from the group consisting of spiral-, zigzag-, dot- and stripe-patterns. Application of the adhesive in such patterns defines the adhesive-coated zones and the adhesive-free zones in the first backsheet 2 and the topsheet 3.

Figure 3:
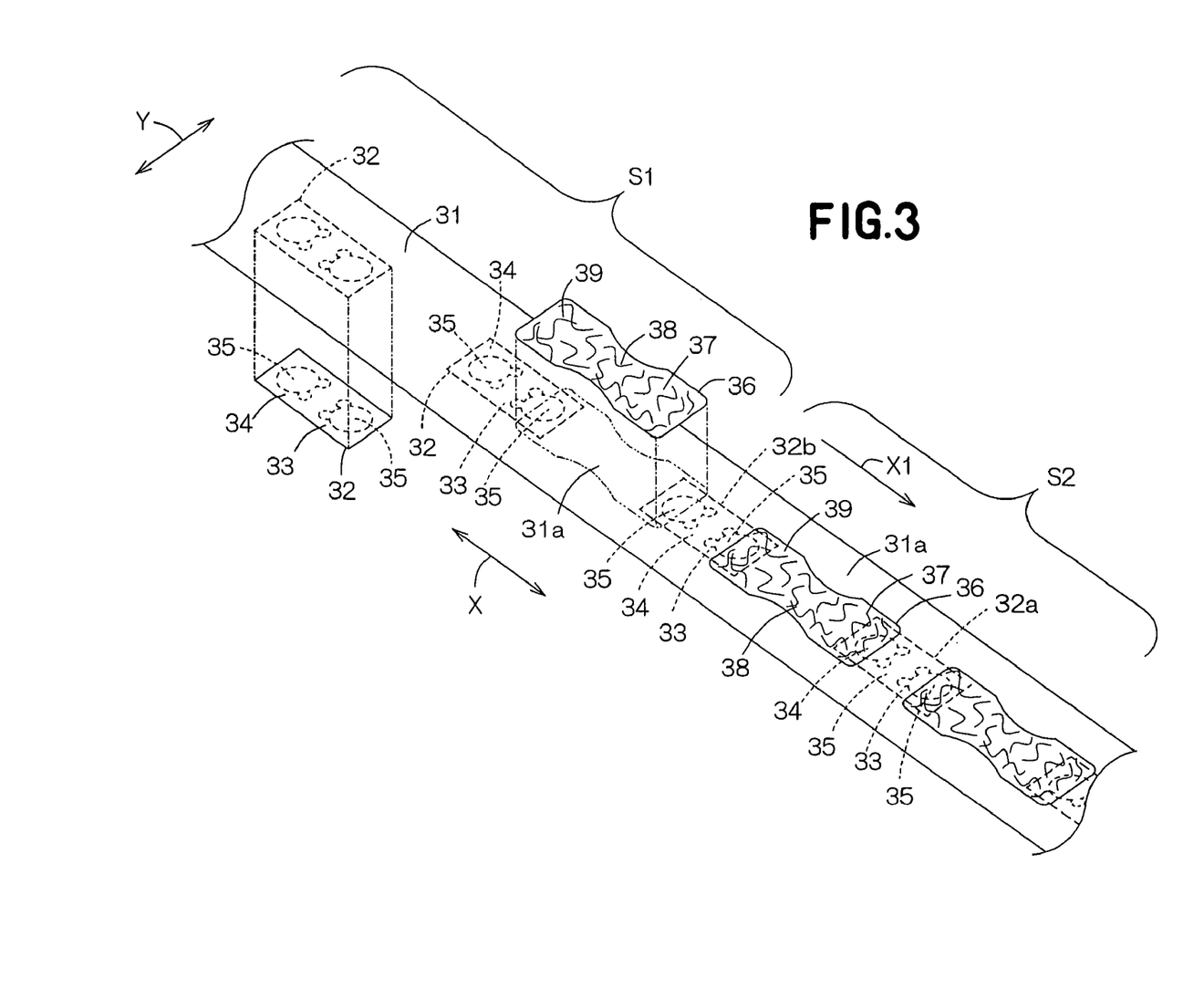
FIG. 3 is a perspective view schematically illustrating an embodiment of the process for forming an indicator element.
Figure 4:
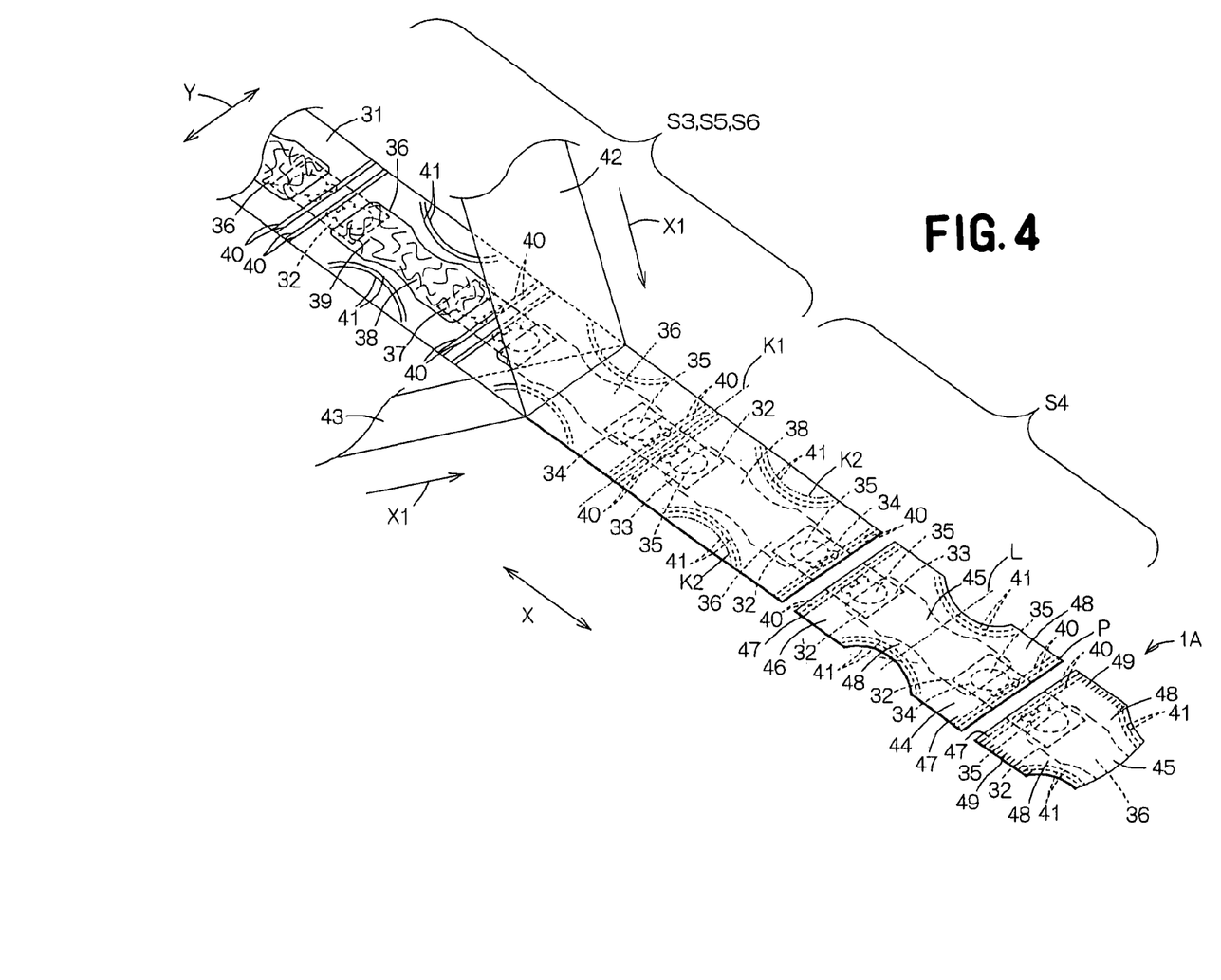
FIG. 4 is a perspective view schematically illustrating steps subsequent to the steps in the process illustrated in FIG. 3.

FIG. 3 is a perspective view schematically illustrating an embodiment of the process for forming the indicator element, FIG. 4 is a perspective view schematically illustrating the steps subsequent to the steps in the process illustrated in FIG. 3. In FIGS. 3 and 4, a machine direction is indicated by an arrow X and a cross direction is indicated by an arrow Y. According to this process, the diaper 1A (laminated panel) of FIG. 1 is manufactured and the indicator element 20 (See FIG. 1) is formed in the front and rear waist regions 6, 8 (front and rear regions) of the diaper 1A through the successive steps as will be described.

Step of feeding members S1: In the step of feeding members S1, a plurality of indication sheets 32 each extending in the machine direction are fed at regular intervals onto an outer surface of a first outer layer web 31 (first backsheet) running in the machine direction while a plurality of the liquid-absorbent cores 36 each extending in the machine direction are fed at regular intervals onto an inner surface of the first outer layer web 31.

The outer layer web 31 run forward in the machine direction indicated by an arrow X1 at a constant speed. The outer layer web 31 is formed by moisture-permeable and hydrophobic fibrous nonwoven fabric. The indication sheet 32 is formed by moisture-permeable and liquid-impervious plastic film.

Each of the indication sheets 32 is in form of a rectangle, of which the long sides extend in the machine direction, and has front half 33 and a rear half 34. The indication sheet 32 is provided in the front and rear end halves 33, 34 with a pair of indicator elements 35, respectively. The indicator elements 35 comprise illustrations of bears' faces printed on an outer surfaces of the indication sheet 32. These illustrated bears' faces are in mirror image relationship with each other in the machine direction. The core 36 has a hourglass-like planar shape and has, as viewed in the machine direction, the front end zone 37, the rear end zone 39 and the intermediate zone 38 extending in the machine direction between these end zones 37, 39.

Step of placing members S2: In the step of placing members S2, the intermediate zone 38 of the core 36 is placed between each pair of the indication sheets 32 adjacent to each other in the machine direction; the rear half 34 of the indication sheet 32a, the front one of these adjacent indication sheets 32 as viewed in the machine direction, is placed upon the front end zone 37 of the core 36; and the front half 33 of the indication sheet 32b, the rear one of these adjacent indication sheets 32 as viewed in the machine direction, is placed upon the rear end zone 39 of the core 36.

In the step of placing members S2, the indication sheets 32 and the cores 36 are arranged at regular intervals in the machine direction on a transversely middle zone 31a of the outer layer web 31. The illustration printed on the rear half 34 of the indication sheet 32 lies in the front end zone 37 of the core 36 and the illustration printed on the front half 33 of the indication sheet 32 lies in the rear end zones 39 of the respective cores 36.

Step of joining members S3: In the step of joining members S3, the indication sheet 32 is joined to the outer surface of the first outer layer web 31 by means of a hot melt adhesive (not shown) and a lower surface of the core 36 is joined to the inner surface of the first outer layer web 31 by means of a hot melt adhesive (not shown).

Then, a plurality of first stretchable elastic members 40 (waist elastic members) lying between each pair of the adjacent cores 36 and extending in the cross direction are attached in a stretched state to the inner surface of the outer layer web 31 while a plurality of second stretchable elastic members 41 (leg elastic members) lying on both sides of the core 36 as viewed in the cross direction and extending in the machine direction are attached in a stretched state to the inner surface of the outer layer web 31 (step of attaching elastic members S5). The first stretchable elastic members 40 extend immediately outside of the front and rear end zones 37, 39 of the core 36 substantially in a straight line. The second stretchable elastic members 41 extend immediately outside of the intermediate zone 38 of the core 36 so as to describe circular arcs which are convex inward as viewed in the cross direction.

After these members 32, 36, 40, 41 are attached, the inner surface of the inner layer web 42 (topsheet) continuously running in the machine direction is placed upon the inner surface of the first outer layer web 31 and the inner surface of the second outer layer web 43 (second backsheet) continuously running in the machine direction is placed upon the outer surface of the first outer layer web 31. The first outer layer web 31 and the inner layer web 42 have respective inner surfaces joined together by means of a hot melt adhesive (not shown). Thereupon, an upper surface of the core 36 and first and second stretchable elastic members 40, 41 are joined to an inner surface of the inner layer web 42. The outer surface of the first outer layer web 31 and the inner surface of the second outer layer web 43 are joined by means of a hot melt adhesive (not shown) (step of joining the outer layer web S6). The indication sheet 32 and the second outer layer web 43 are left free from each other.

The inner layer web 42 and the second outer layer web 43 travel forward in the machine direction as indicated by an the arrow X1 at the same speed as the outer layer web 31. The inner layer web 42 is formed by moisture-permeable and hydrophobic fibrous nonwoven fabric (second fibrous nonwoven fabric). The second outer layer web 43 is formed by moisture-permeable and liquid-impervious plastic film. The adhesive is applied on the entire inner and outer surfaces of the first outer layer web 31 and on the entire inner surface of the inner layer web 42 in spiral-, zigzag-, dot- or stripe-pattern.

In the step of joining members S3, it is possible to join the first and second stretchable elastic members 40, 41 in a stretched state to the outer surface of the first outer layer web 31 or the inner surface of the inner layer web 42. It is also possible to join the first and second stretchable elastic members 40, 41 to the inner surface of the first outer layer web 31 in the step of feeding members S1 or in the step of placing members S2.

Step of forming laminated panels S4: In the step of forming laminated panels S4, the first and second outer layer webs 31, 43, the inner layer web 42 and the indication sheet 32 are cut along each first cutting line K1 extending in the cross direction between each pair of the cores 36 adjacent to each other in the machine direction and thereby the indication sheet 32 is divided into the front half 33 and the rear half 34. In addition, the portions of the first and second outer layer webs 31, 43 and the inner layer web 42 which lie outside the intermediate zone 38 of the core 36 are cut along each second cutting line K2 extending in the machine direction and thereby a plurality of the laminated panels P arranged in the machine direction are obtained. The first cutting line K1 extends between the first stretchable elastic members 40 substantially in a straight line in the cross direction. The second cutting line K2 extends immediately outside the second stretchable elastic members 41 so as to describe circular arcs which are convex inward in the cross direction.

The laminated panel P has a substantially hourglass-like planar shape and is composed of, in the machine direction, a front region 44 (front waist region), a rear region 46 (rear waist region) and an intermediate region 45 (crotch region). The laminated panel P includes end flaps 47 extending in the cross direction and side flaps 48 extending in the machine direction. The laminated panel P is formed in the front and rear regions 44, 46 with indicator elements 35, respectively, which are visually recognizable from an exterior of the panel P.

The laminated panel P may be folded along a transverse fold guiding line L bisecting a length of the panel P with the inner layer web 42 inside and then the side flaps 48 in the front and rear regions 44, 46 overlaid may be joined together by means of heat-sealing lines 49 to obtain the pull-on diaper 1A shown in FIG. 1.

Figure 5:
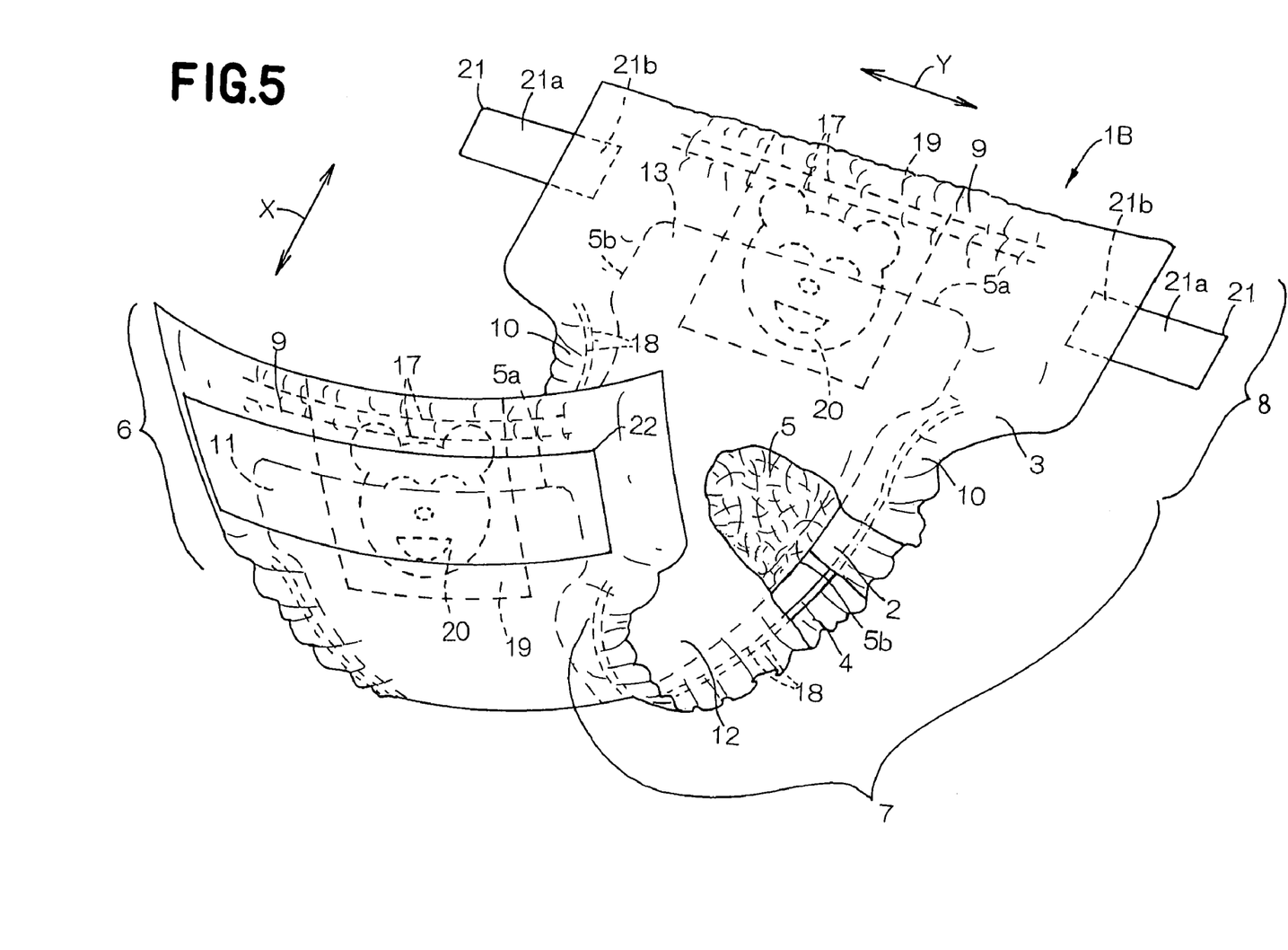
FIG. 5 is a partially cutaway perspective view showing an pull-on disposable diaper.
Figure 6:
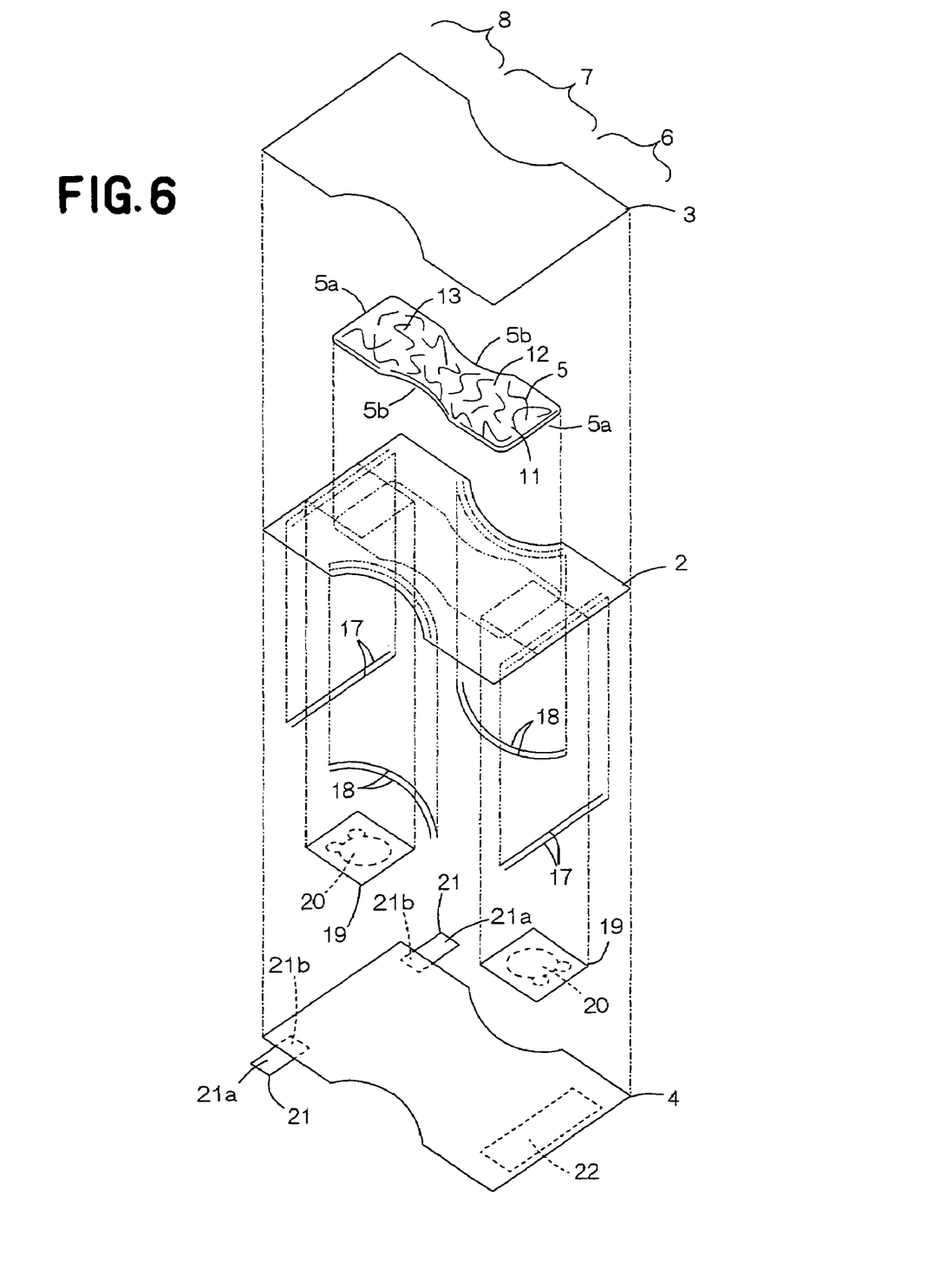
FIG. 6 is an exploded perspective view showing the diaper of FIG. 5.

FIG. 5 is a partially cut away perspective view showing an pull-on disposable diaper 1B manufactured through the process for indicator element formation as will be described below and FIG. 6 is an exploded perspective view showing the diaper 1B showing in FIG. 5. In FIGS. 5 and 6, a vertical direction (longitudinal direction) is indicated by an arrow X and a transverse direction is indicated by an arrow Y.

This diaper 1B comprises a laminated panel and is of open-type and is disposable after used. The diaper 1B comprises a liquid-impervious first backsheet 2 (first outer layer web) and a liquid-impervious second backsheet 4 (second outer layer web) both lying on the side facing away from a wearer's body, a liquid-pervious topsheet 3 (inner layer web) lying on the side facing the wearer's body and a liquid-absorbent core 5 interposed between the top- and backsheets 2, 3.

The diaper 1B is composed of a front waist region 6 (front region) and a rear waist regions 8 (rear region) opposed to each other and a crotch region 7 (intermediate region) extending between these waist regions 6, 8. The diaper 1B has end flaps 9 lying outside longitudinally opposite ends 5a of the core 5 and extending in the transverse direction and side flaps 10 lying outside transversely opposite side edges 5b of the core 5 and extending in the longitudinal direction. The diaper 1B has a generally hourglass-like planar shape. The core 5 extends over the crotch region 7 into the front and rear waist regions 6, 8. The core 5 has front and rear end zones 11, 13 lying in the front and rear waist regions 6, 8, respectively, and an intermediate zone 12 lying in the crotch region 7.

A plurality of waist elastic members 17 (first stretchable elastic members) extending in the transverse direction are contractibly attached to the end flaps 9. A plurality of leg elastic members 18 (second stretchable elastic members) extending in the longitudinal direction are attached to the side flaps 10 in the crotch region 7. These elastic members 17, 18 are interposed between the first and second backsheets 2, 4. The first and second backsheets 2, 4 are formed by moisture-permeable and hydrophobic fibrous nonwoven fabric.

The topsheet 3 is formed by hydrophilic fibrous nonwoven fabric. The core 5 is the same as that shown in FIG. 1.

The front and rear waist regions 6, 8 are provided in respective transversely middle zones thereof with indication sheets 19 each having an indicator element 20 adapted to be visually recognized from an exterior of the diaper 1B. The indication sheet 19 is made of moisture-permeable and hydrophobic fibrous nonwoven fabric. The indicator element 20 comprises an illustration of a bear's face printed on an outer surface of the indication sheet 19. These illustrations are placed in the front and rear end zones 11, 13 of the core 5, respectively.

The end flaps 9 are formed by respective portions of the first and second backsheets 2, 4 and the topsheet 3 extending outward in the longitudinal direction beyond the longitudinally opposite ends 5a of the core 5. The side flaps 10 are formed by respective portions of the first and second backsheets 2, 4 and the topsheet 5 extending outward in the transverse direction beyond the transversely opposite side edges 5b of the core 5.

The second backsheet 4 is placed on and intermittently joined to the outer surface of the first backsheet 2 by means of a hot melt adhesive (not shown). The indication sheet 19 is interposed between the first and second backsheets 2, 4 and has its inner surface intermittently joined to the outer surface of the backsheet 2 by means of a hot melt adhesive (not shown) The indication sheet 19 is left free from the backsheet 4.

In the end flaps 9 as well as in the side flaps 10, the first backsheet 2 and the topsheet 3 are overlaid and have the respective inner surfaces intermittently bonded by means of a hot melt adhesive (not shown). The core 5 is intermittently joined to the respective inner surfaces of the first backsheet 2 and the topsheet 3 by means of a hot melt adhesive (not shown). The elastic members 17, 18 are intermittently joined to the outer surface of the first backsheet 2 by means of a hot melt adhesive (not shown). The adhesive is applied on the entire inner and outer surfaces of the first backsheet 2 and the entire inner surface of the topsheet 3 in a pattern selected from the group consisting of spiral-, zigzag-, dot- and stripe-patterns.

The side flaps 10 in the rear waist region 8 are respectively provided with tape fasteners 21 attached thereto and extending outward in the transverse direction. Each of the tape fasteners 21 has a free end zone 21a coated with a pressure-sensitive adhesive (not shown) and a proximal end zone 21b fixed to the outer surface of the second backsheet 4. The pressure-sensitive adhesive is protectively covered with a release paper (not shown). The second backsheet 4 in the front waist region 6 is provided on its outer surface with a target tape strip 22 attached thereto so that the free end zone 21a of the tape fastener 21 may be releasably anchored on this target tape strip 22. The tape fastener 21 as well as the target tape strip 22 is formed by flexible plastic film.

To put this diaper 1B on the wearer's body, the side flaps 10 in the rear waist region 8 are placed upon the outer side of the side flaps 10 in the front waist region 6, then the free end zones 21a of the respective tape fasteners 21 are anchored on the target tape strip 22 and thereby the front and rear waist regions 6, 8 are connected with each other. Thereupon the diaper 1B is formed with the waist-hole and a pair of the leg-holes below the waist-hole.

Figure 7:
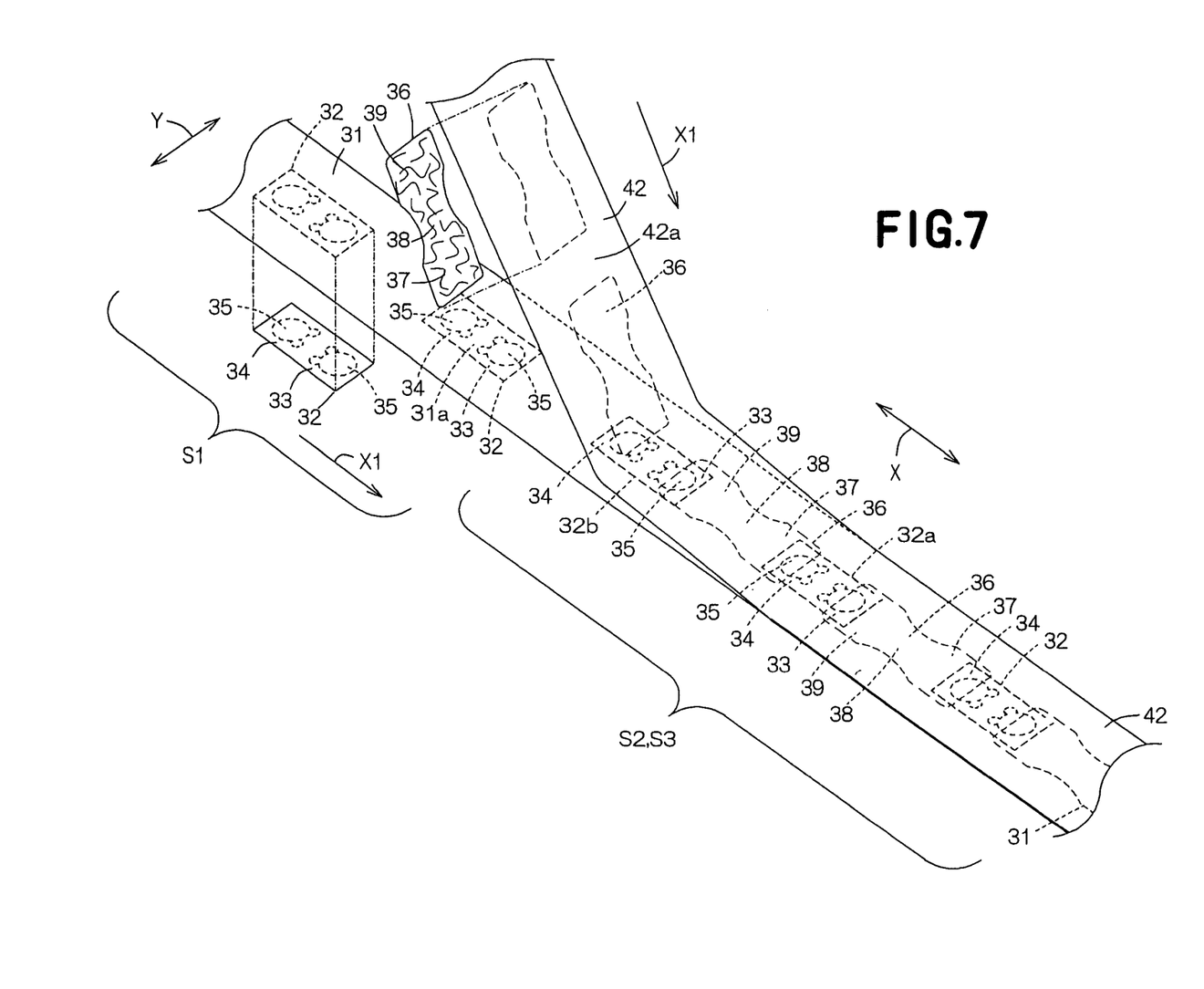
FIG. 7 is a perspective view schematically illustrating another embodiment of the process for forming an indicator element.
Figure 8:
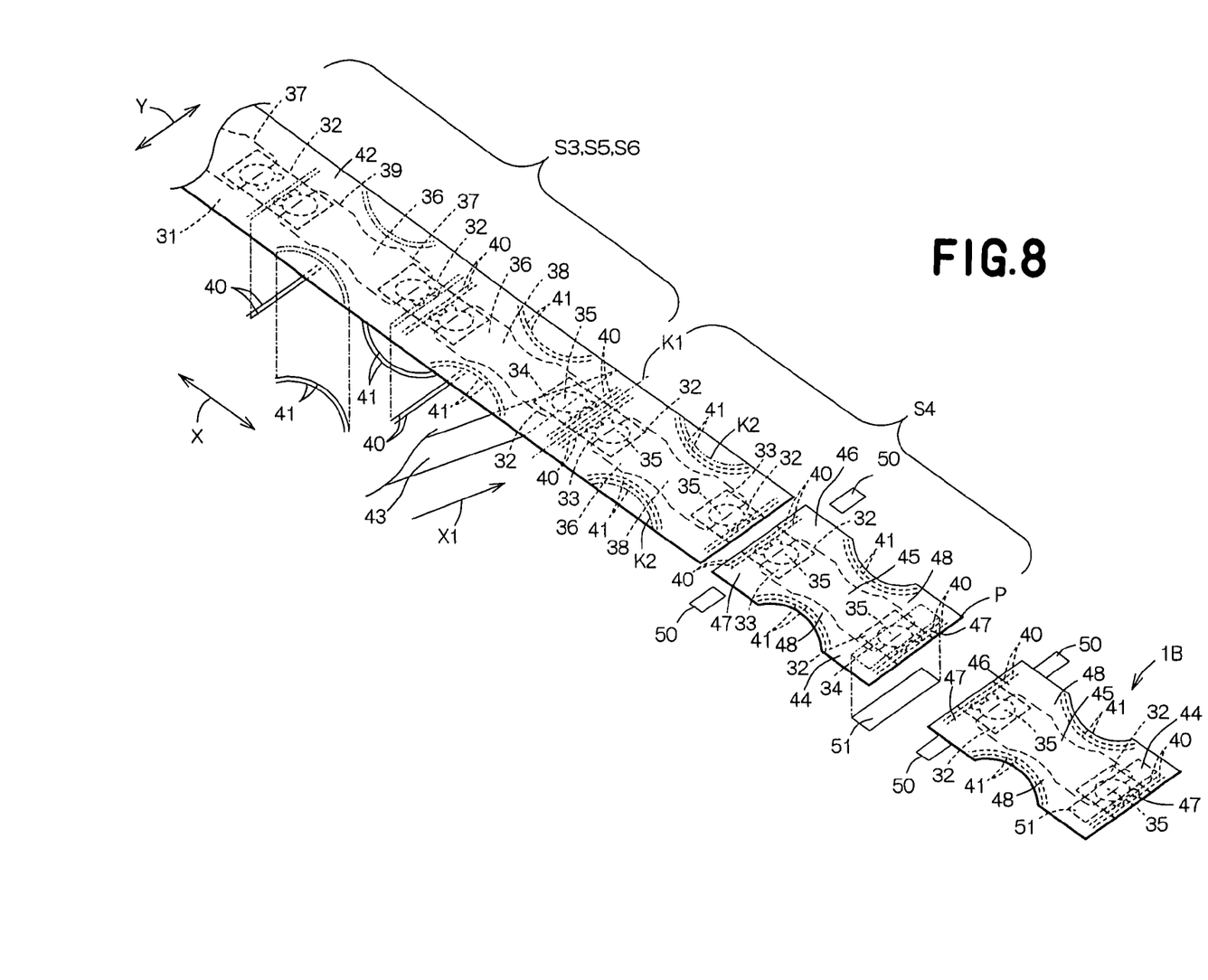
FIG. 8 is a perspective view schematically illustrating steps subsequent to the steps in the process illustrated in FIG. 7.

FIG. 7 is a perspective view schematically illustrating another embodiment of the process for forming the indicator element and FIG. 8 is a perspective view schematically illustrating the steps subsequent to the steps in the process illustrated in FIG. 7. In FIGS. 7 and 8, a machine direction is indicated by an arrow X and a cross direction is indicated by an arrow Y. According to this process, the diaper 1B (laminated panel) of FIG. 5 is manufactured and the indicator elements 20 (See FIG. 5) are formed in the front and rear waist regions 6, 8 (front and rear regions) of the diaper 1B through the successive steps as will be described.

Step of feeding members S1: In the step of feeding members S1, a plurality of indication sheets 32 each extending in the machine direction are fed onto an outer surface of first outer layer web 31 (first backsheet) running in the machine direction while a plurality of the liquid-absorbent cores 36 each extending in the machine direction are fed at regular intervals onto an inner surface of the inner layer web 42 continuously running in the machine direction.

The outer layer web 31 and the inner layer web 42 run forward in the machine direction indicated by an arrow X1 at a constant speed. The outer layer web 31 is formed by moisture-permeable and hydrophobic fibrous nonwoven fabric. The inner layer web 42 is formed by hydrophilic fibrous nonwoven fabric. The indication sheet 32 is formed by moisture-permeable and hydrophobic fibrous nonwoven fabric.

Each of the indication sheets 32 is in form of a rectangle, of which the long sides extend in the machine direction, and has front half 33 and a rear half 34. The indication sheet 32 is provided in the front and rear end halves 33, 34 with a pair of indicator elements 35, respectively. The indicator element 35 comprises illustration of a bear's face printed on an outer surface of the indication sheet 32. These illustrated bears' faces of the indication sheet 32. These illustrations are in mirror image relationship with each other in the machine direction. The core 36 has a hourglass-like planar shape and has, as viewed in the machine direction, the front end zone 37, the rear end zone 39 and the intermediate zone 38 extending in the machine direction between these end zones 37, 39.

Step of placing members S2: In the step of pacing members S2, the intermediate zone 38 of the core 36 is placed between each pair of the indication sheets 32 adjacent to each other in the machine direction; the rear half 34 of the indication sheet 32a, the front one of these adjacent indication sheets 32 as viewed in the machine direction, is placed upon the front end zone 37 of the core 36; and the front half 33 of the indication sheet 32b, the rear one of these adjacent indication sheets 32 as viewed in the machine direction, is placed upon the rear end zone 39 of the core 36.

In the step of placing members S2, the indication sheets 32 are arranged at regular intervals in the machine direction in a transversely middle zone 31a of the outer layer web 31 and the cores 36 are arranged at regular intervals in the machine direction in a transversely middle zone 42a of the inner layer web 42. The illustration printed on the rear half 34 of the indication sheet 32 lies in the front end zone 37 of the core 36 and the illustration printed on the front half 33 of the indication sheet 32 lies in the rear end zone 39 of the core 36.

Step of joining members S3: In the step of joining members S3, the indication sheet 32 is joined to the inner surface of the first outer layer web 31 by means of a hot melt adhesive (not shown) and an upper surface of the core 36 is joined to the inner surface of the inner layer web 42 by means of a hot melt adhesive (not shown). In addition, the inner surface of the first outer layer web 31 and the inner surface of the inner layer web 42 are overlaid and joined together by means of a hot melt adhesive (not shown). At the same time, a lower surface of the core 36 is joined to the first outer layer web 31.

Then, a plurality of first stretchable elastic members 40 (waist elastic members) lying between each pair of the adjacent cores 36 and extending in the cross direction are attached in a stretched state to the outer surface of the outer layer web 31 while a plurality of second stretchable elastic members 41 (leg elastic members) lying on both sides of the core 36 as viewed in the cross direction and extending in the machine direction are attached in a stretched state to the outer surface of the outer layer web 31 (step of attaching elastic members S5). The first stretchable elastic members 40 extend immediately outside of the front and rear end zones 37, 39 of the core 36 substantially in a straight line. The second stretchable elastic members 41 extend immediately outside of the intermediate zone 38 of the core 36 so as to describe circular arcs which are convex inward as viewed in the cross direction. In the step of the joining members S3, it is possible to attach the first and second stretchable elastic members 40, 41 in a stretched state to the inner surface of the first outer layer web 31 or the inner surface of the inner layer web 42.

After these members 32, 36, 40, 41 are attached, the inner surface of the second outer layer web 43 (second backsheet) continuously running in the machine direction is placed upon the outer surface of the first outer layer web 31. The outer surface of the first outer layer web 31 and the inner surface of the second outer layer web 43 are joined together by means of a hot melt adhesive (not shown) (step of joining the outer layer web S6). The indication sheet 32 and the second outer layer web 43 are left free from each other.

The second outer layer web 43 runs forward in the machine direction indicated by the arrow X1 at the same speed as the first outer layer web 31 and the inner layer web 42. The second outer layer web 43 is formed by moisture-permeable and hydrophobic fibrous nonwoven fabric. The adhesive is applied on the entire inner and outer surfaces of the first outer layer web 31 and on the entire inner surface of the inner layer web 42 in spiral-, zigzag-, dot- or stripe-pattern.

Step of forming laminated panels S4: In the step of forming laminated panels S4, the first and second outer layer webs 31, 43, the inner layer web 42 and the indication sheet 32 are cut along each first cutting line K1 extending in the cross direction between each pair of the cores 36 adjacent to each other in the machine direction and thereby the indication sheet 32 is divided into the front half 33 and the rear half 34. In addition, the portions of the first and second outer layer webs 31, 43 and the inner layer web 42 which lie outside the intermediate zone 38 of the core 36 are cut along each second cutting line K2 extending in the machine direction and thereby a plurality of the laminated panels P arranged in the machine direction are obtained. The first cutting line K1 extends between the first stretchable elastic members 40 substantially in a straight line in the cross direction. The second cutting line K2 extends immediately outside the second stretchable elastic members 41 so as to describe circular arcs which are convex inward in the cross direction.

The laminated panel P has a substantially hourglass-like planar shape and is composed of, in the machine direction, a front region 44 (front waist region), a rear region 46 (rear waist region) and an intermediate region 45 (crotch region). The laminated panel P includes end flaps 47 extending in the cross direction and side flaps 48 extending in the machine direction. The laminated panel P is formed in the front and rear regions 44, 46 with indicator elements 35, respectively, which are visually recognizable from an exterior of the panel P.

Then, tape fasteners 50 are attached to the side flaps 48 in the rear region 46 so as to extend outward in the cross direction and a rectangular target tape strip 51 is attached to the outer surface of the second outer layer web 43 in the front region 44 so as to extend in the cross direction. In this way, the open-type diaper 1B shown in FIG. 5 is obtained. The tape fasteners 50 have the proximal end zones thereof fixed to the outer surface of the second outer layer web 43.

A stock material for the first and second outer layer webs 31, 43 may be selected from the group consisting of a composite nonwoven fabric comprising two layers of moisture-permeable and hydrophobic fibrous nonwoven fabrics laminated with each other and a composite sheet comprising a moisture-permeable and hydrophobic fibrous nonwoven fabric and a moisture-permeable and liquid-impervious plastic film. A stock material for the inner layer web 42 may be selected from the group consisting of a hydrophobic fibrous nonwoven fabric having a plurality of apertures and a plastic film having a plurality of fine apertures.

The fibrous nonwoven fabric may be selected from the group consisting of those obtained by spun lace-, needle punch-, melt blown-, thermal bond-, spun bond-, chemical bond- and air through-processes. The component fibers of the nonwoven fabric may be selected from the group consisting of polyolefin-, polyester- and polyamide-based fibers and core-and-sheath or side-by-side conjugated fibers of polyethylene/polypropylene or polyethylene/polyester.

Preferably, polyolefin-based thermoplastic synthetic resin is used as a stock material for the plastic film. This film preferably has a moisture-permeability in a range of 2150 to 4000 $g/m^2 \cdot 24$ hrs.

The laminated panel P is applicable to, in addition to the pull-on disposable diaper 1A having its front and rear waist regions 6, 8 previously connected with each other and the open-type disposable diaper 1B having its front and rear waist regions 6, 8 connected with each other immediately before put on the wearer's body, to an absorbent pad adapted to be attached to inner surface of diaper cover.

The process according to this invention for forming the indicator element is primarily characterized in that the indication sheet having a pair of indicator elements on the front and rear regions, respectively, is divided in two so that the indicator elements can be formed on the front and rear regions of the panel all at once in the course of manufacturing a plurality of the laminated panels arranged in the machine direction. This process makes it unnecessary to use means as well as steps for separately attaching the individual indicator elements to the front and rear waist regions. In this way, the indicator elements on the front and rear regions of the laminated panels can be continuously formed at a high speed, on one hand, and at a low cost, on the other hand.

According to this process, the indication sheet having a pair of the illustrations printed on the indication sheet are in the mirror image relationship with each other in the machine direction and therefore there is no possibility that one of these illustrations respectively formed on the front and rear regions might be placed upside down with respect to the other illustration.

What is claimed is:

1. A process of attaching indicator elements to front and rear regions of a disposable garment comprising a laminated panel which comprises an outer layer web lying on a side adapted to face away from a wearer's body in use, an inner layer web lying on a side adapted to face said wearer's body in use, and a liquid-absorbent core interposed between said outer layer web and said inner layer web, said indicator elements being visible from an exterior of said panel, said process comprising the steps of:

feeding a plurality of indication sheets each extending in a machine direction and having said indicator elements in front and rear halves thereof, at regular intervals onto a continuous first outer layer web running in said machine direction, while feeding a plurality of said liquid-absorbent cores each extending in said machine direction and having a front end zone, a rear end zone and an intermediate zone, at regular intervals onto one of an inner surface of said continuous first outer layer web and an inner surface of a continuous inner layer web running in said machine direction;

placing said intermediate zone of one said core between each pair of said indication sheets adjacent to each other in said machine direction so that the rear half of a front one of said adjacent indication sheets is placed upon said front end zone of said core, and a front half of a rear one of said adjacent indication sheets is placed upon said rear end zone of said core;

joining each said indication sheet to said first outer layer web, joining each said core to at least one of said inner layer web and said first outer layer web, and joining inner surfaces of said inner layer web and said first outer layer web which are overlaid upon each other; and cutting said indication sheets together with said inner and first outer layer webs in a cross direction between each pair of said cores adjacent to each other in said machine direction, so that each said indication sheet is divided into said front and rear halves to form a plurality of said laminated panels arranged in said machine direction and having said indicator elements in the respective front and rear regions.

2. The process according to claim 1, further comprising the steps of placing an inner surface of a continuous second outer layer web running in said machine direction upon said outer surface of said first outer layer web; and joining said first and second outer layer webs;

wherein, at the cutting step, each said indication sheet is cut together with said first and second outer layer webs and said inner layer web in said cross direction between the respective pair of adjacent cores.

3. The process according to claim 1, further comprising the step of attaching first and second stretchable elastic members in a stretched state to said inner surface of said first outer layer web or said inner layer web;

said first stretchable elastic members lying between said adjacent cores and extending in said cross direction; and said second stretchable elastic members lying on both lateral sides of each said core and extending in said machine direction.

4. The process according to claim 2, further comprising the step of attaching first and second stretchable elastic members in a stretched state to said outer surface of said first outer layer web or said inner surface of said second outer layer web;

said first stretchable elastic members lying between said adjacent cores and extending in said cross direction; and said second stretchable elastic members lying on both lateral sides of each said core and extending in the machine direction.

5. The process according to claim 2, wherein said first and second outer layer webs are formed by one of (i) a moisture-permeable and hydrophobic fibrous nonwoven fabric and (ii) a moisture-permeable and liquid-impervious plastic film; and said inner layer web is formed by a hydrophilic fibrous nonwoven fabric.

6. The process according to claim 1, wherein each said indication sheet is formed by one of (i) a moisture-permeable and hydrophobic fibrous nonwoven fabric and (ii) a moisture-permeable and liquid-impervious plastic film.

7. The process according to claim 1, wherein said indicator elements comprise a pair of illustrations respectively printed on said the front and rear halves of the respective indication sheet and adjacent to each other in said machine direction.

8. The process according to claim 7, wherein said illustrations are in mirror image relationship with each other in said machine direction.

* * * * *